United States Patent [19]
Voudouris

[11] Patent Number: 5,474,445
[45] Date of Patent: Dec. 12, 1995

[54] SELF-ENGAGING TWIN EDGE-WISE ORTHODONTIC BRACKET WITH PIVOTAL LATCH

[75] Inventor: John Voudouris, 44 St. Joseph Street, Suite 1714, Toronto, Ontario, Canada, M4Y 2W4

[73] Assignee: John Voudouris

[21] Appl. No.: 206,724

[22] Filed: Mar. 7, 1994

[51] Int. Cl.⁶ .................................................. A61C 3/00
[52] U.S. Cl. ................................. 435/10; 433/11
[58] Field of Search ................... 433/10, 11, 13, 433/14

[56] References Cited

U.S. PATENT DOCUMENTS

| | | | |
|---|---|---|---|
| 3,091,857 | 6/1963 | Rubin et al. | 433/11 |
| 4,103,423 | 8/1978 | Kessel | 433/10 |
| 4,149,314 | 4/1979 | Nonnenmann | 433/13 |
| 4,698,017 | 10/1987 | Hanson | 433/11 |
| 4,712,999 | 12/1987 | Rosenberg | 433/11 |
| 5,224,858 | 7/1993 | Hanson | 433/10 |
| 5,269,681 | 12/1993 | Degnan | 433/11 |

*Primary Examiner*—Cary E. O'Connor
*Attorney, Agent, or Firm*—Sim & McBurney

[57] ABSTRACT

A self-engaging twin edgewise orthodontic bracket, comprising a body portion having a lingual surface for attachment to a tooth, a pair of gingival and occlusal tie wings extending buccal (or labially) from the lingual surface, a central mesiodistally extending labially opening slot for receiving an archwire, a second superior and labial interrupted mesial and distal slot, a first mesiodistally extending stepped, lingual locking surface intermediate of the gingival or occlusal tie wings, and a mesiodistally extending axis intermediate the other of the gingival or occlusal tie wings; a pivotal latch having a catch at one end thereof for locking engagement with the locking surface, a pivot at an opposite end thereof for pivotally receiving the axis such that the latch is pivotal from an open position for inserting and removing the archwire to a closed position wherein the latch covers the slot and the catch is positioned gingivally of the locking surface, and latching apparatus adjacent the pivot and intermediate the one end and the opposite end for receiving the axis such that the catch securely engages the locking surface in the closed position thereby retaining the archwire in the slot.

15 Claims, 7 Drawing Sheets

SELF-ENGAGING TWIN EDGE-WISE ORTHODONTIC BRACKET WITH PIVOTAL LATCH

FIELD OF THE INVENTION

The present invention relates in general to orthodontic appliances, and more particularly to a self-engaging twin edgewise orthodontic bracket with improved pivotal latch.

BACKGROUND OF THE INVENTION

According to established orthodontic techniques, it is well known that one is able to ligate an archwire to a bracket utilizing an elastic or metal ligature. In a twin edgewise bracket, the elastic ligature is stretched around respective undercuts of gingival and occlusal tie wings so as to overlay the archwire at mesial and distal ends of the bracket.

The ligating procedure involves carefully stretching the elastic ligature (or wrapping and twisting a metal ligature) around the tie wings utilizing appropriate orthodontic instruments. It has been found that the time consuming ligation procedure contributes to lengthy chair time. Furthermore, the elastic ligatures are known to lose their elasticity with time and are subject to degradation. Also, the elastic and metal ligatures have been known to trap food particles in areas of the bracket which are difficult for the patient to clean, and to increase the level of friction against the archwire. Finally, the use of sharp metal ligatures around the bracket can subject the clinician to unnecessary exposure to infectious bacteria, or viruses such as hepatitis B, or possibly the HIV virus in blood.

In an effort to overcome these disadvantages of elastic ligatures, certain advances have been made in the area of self-engaging brackets. Each of U.S. Pat. Nos. 4,144,642; 4,248,588; 4,698,017; 3,772,787; 4,786,252; 4,559,012; 4,561,844; 4,655,708; 4,077,126; 4,419,078; 4,634,662; 4,197,642 and 4,712,999 illustrate one or more designs for self-engaging brackets.

Furthermore, my own U.S. patent application Ser. No. 08/007,095 filed on Jan. 21, 1993, and entitled Self-Engaging Orthodontic Bracket, describes an improved self-engaging twin orthodontic bracket having a generally U-shaped locking shutter which is slidably received in the base member of the bracket. These prior art devices overcome some of the disadvantages associated with elastic ligatures. Self-engaging brackets eliminate, or at least reduce exposure of the clinician to sharp ligatures, thereby alleviating the problem of contracting dangerous viruses. In addition, self-engaging brackets permit differential archwire contact separately for round and rectangular archwires at two different levels of contact, which is not possible with elastic or metal ligatures which interact with all individual archwires in a similar manner. However, most of the known prior art self-engaging brackets lack the reliability and ease of operability that most clinicians require.

SUMMARY OF THE INVENTION

According to the present invention, a self-engaging twin edgewise orthodontic bracket is provided having a pivotal latch for securing an orthodontic archwire. Although U.S. Pat. Nos. 4,634,662 and 4,712,999 and U.S. Pat. No. 4,559,012 disclose the use of a pivotal latch for securing an archwire, there is no provision for movement of the pivotal shutter in an occlusal-gingival direction and the twin tie-wing undercuts are obstructed.

According to the preferred embodiment of the present invention, the pivotal latch is provided with a hook-shaped catch at one end, and a mesial-distally extending pivot pin at an opposite end, and is positioned between the tie wings from a frontal view. In one embodiment, the pivotal latch is connected to the side of the bracket where the single mesial distal pivot pin protrudes at the sides of the bracket so that the tie wing undercuts are open and free. This allows for straightforward addition of auxiliary attachments, where necessary, such as an elastic chain between the brackets. A semi-rigid generally figure-eight shaped latch portion (side view) is provided adjacent the pivot in order that the latch may be moved vertically over the pivot bar to pivot between open and closed positions for installing and removing the archwire. In the initial closed position the hook-shaped catch is initially positioned above a locking surface of the bracket such that the pivot pin extends through a lower channel of the figure-eight shaped latch portion. The latch may then be pushed in an occlusal direction so as to lock the pivotal latch in a final closed position between the hook-shaped catch and the latching portion, wherein the pivot pin is received in an upper channel of the figure-eight shaped latch portion. Similarly, in order to unlock the bracket for removing an archwire, the pivotal latch is moved in a gingival direction for lifting the hook-shaped catch above the bracket locking surface and positioning the lower channel of the latch on the pivot pin for opening the latch.

A number of advantages are obtained over the prior art by providing the semi-rigid pivotal latch of the present invention in a forward or labial position relative to the bracket pad. Specifically, the flexibility of the semi-rigid figure-eight shaped latch portion allows the pivotal latch to flex over the pivot pin during opening and closing. Also, by having the opening and closing portions of the latch on the labial face of the bracket, the clinician is given easier access to the bracket for opening and closing the pivotal latch. The clinician is better able to mulch tartar build-up upon opening the latch in situations where this build-up binds the latch to the bracket body, and the clinician is given better access for cleaning tartar on the labially attached latch.

According to one aspect of the invention, two levels of contact are provided for (1) initial archwires wherein the hook-shaped catch is connected at a deep lingual step position, and (2) final archwires wherein the catch is positioned labial to the deep lingual step position and slightly gingival to the deep lingual step position.

According to another aspect of the invention, a special twin bracket is provided with reduced mesial and distal contact of the bracket with the archwire by incorporating a bracket body such as disclosed in U.S. Pat. No. 5,067,897 (Tuneberg), in order to increase the distance between brackets and thereby further increase the flexibility of the archwire. In one embodiment, the pivotal latch is made to extend to a lesser extent mesiodistally, and in another embodiment the pivotal latch is made to extend further mesiodistally.

According to a further aspect of the invention, a spring is wrapped around the pivot and the latch is wrapped around the spring to assist the latch in closing forcefully. To open the latch, the catch is lifted up and pivots occlusally to open. To lock the latch in the open slot position, the latch horizontal component occlusal end (frontal view) steps over a lock notch.

According to yet another embodiment of the invention, the spring is wrapped around the outside of the pivot bar wherein the pivotal latch continues to be connected to the side of the bracket.

The pivot pins in all of the various embodiments may be interrupted mesio-distally or continuously extending mesio-distally.

BRIEF DESCRIPTION OF THE DRAWINGS

A preferred embodiment of the invention is described in detail below with reference to the following drawings, in which.

DETAILED DESCRIPTION OF THE PREFERRED EMBODIMENT

Figure 3:
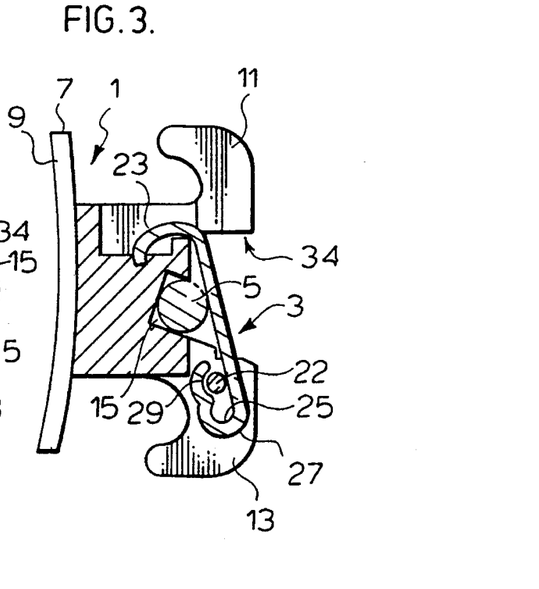
FIG. 3 is a cross-sectional view through the line 3—3 in FIG. 1.
Figure 4A:
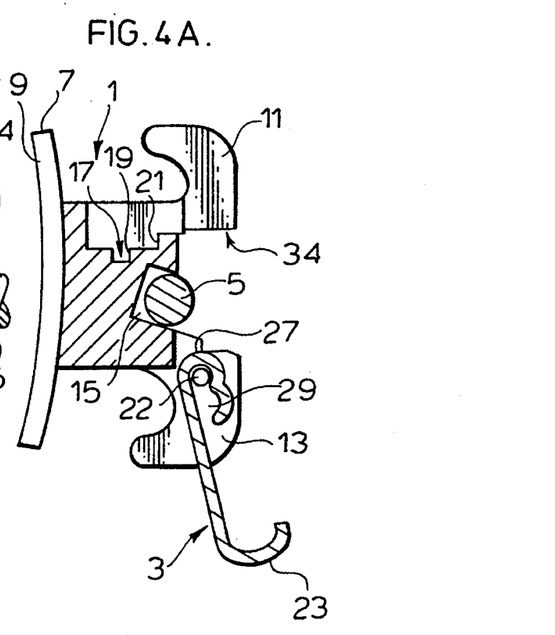
FIG. 4A is a cross-sectional view through the lines 4A—4A in FIG. 2, and FIGS. 4B and 4C are cross-sectional views similar to that of FIG. 4A showing the pivotal latch in intermediate positions between the open position of FIG. 4A and the closed position of FIGS. 1 and 3.
Figure 4B:
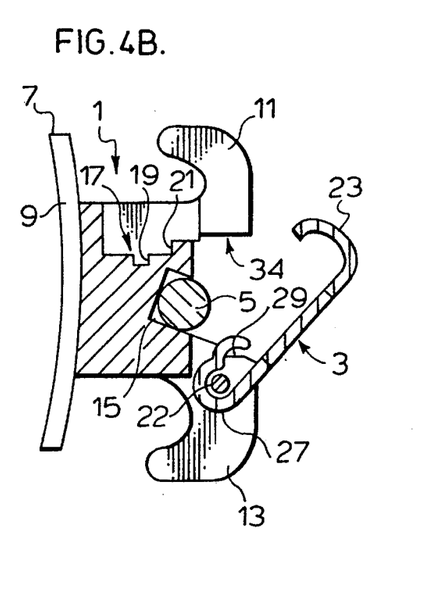
Figure 4C:
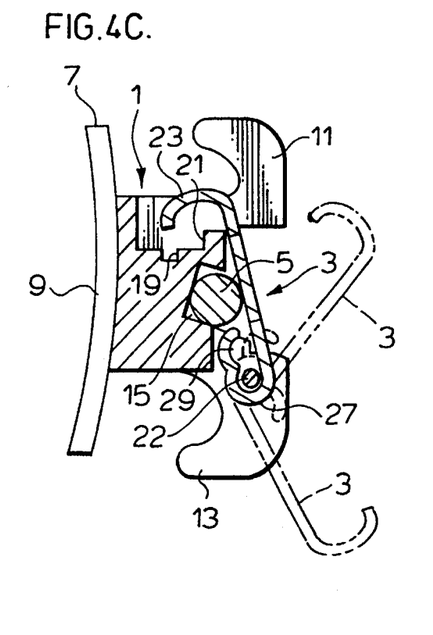
Figures 5, 6:
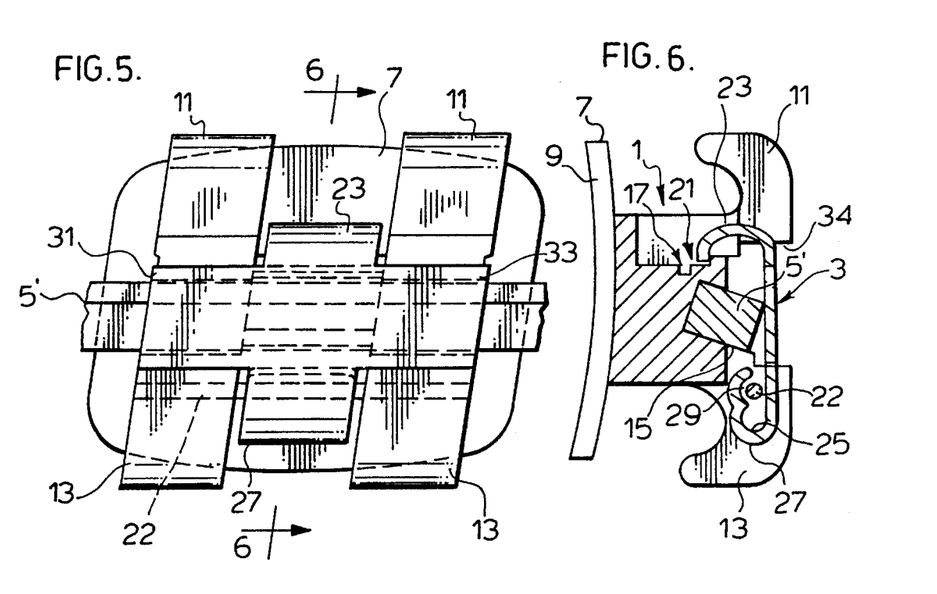
FIG. 5 is a front elevation view of the bracket according to the present invention in a secondary labial locking position for receiving a rectangular archwire.
FIG. 6 is a cross-sectional view along the line 6—6 in FIG. 5.

With reference to FIGS. 1–6, an orthodontic bracket is illustrated according to the preferred embodiment for application to an upper tooth, although the same principles apply for brackets adapted for use with lower teeth. The bracket comprises a body portion 1 and a pivotal latch 3 for securing a circular cross-section archwire 5 as shown in FIGS. 1–4, or a rectangular cross-section archwire 5' as shown in FIGS. 5 and 6.

The body portion 1 includes a lingual portion 7 for attachment to a tooth by means of a mounting pad 9 or other suitable means. A pair of gingival tie wings 11 and a pair of occlusal tie wings 13 extend from the base in a buccal-labial direction. An archwire slot 15 extends mesiodistally across the body portion 1 and opens labially for receiving the archwire 5 or 5'.

As discussed in greater detail below with reference to the pivotal latch 3, in the preferred embodiment body portion 1 includes a generally rectangular groove 17 extending mesiodistally between gingival wings 11 and opening in a gingival direction. The groove 17 provides a first lingual locking surface 19 for the pivotal latch 3. According to the preferred embodiment, a second lingual locking surface 21 is provided in a more labial and gingival direction than the first locking surface 17, as discussed in greater detail below with reference to FIGS. 5 and 6.

According to the preferred embodiment, the body portion 1 also includes a mesiodistally extending cylindrical pivot axis or pivot pin 22 between the occlusal tie wings 13. The axis or pin 22 serves both as a pivoting axis for the latch 3 as well as a latching surface for securing the pivotal latch 3 in a closed position, as discussed in greater detail below. In the preferred embodiment, the axis or pin 22 is in the form of a cylindrical pin which is similar to the pins used to secure wrist bands to watches.

According to the preferred embodiment, pivotal latch 3 is generally in the shape of a "J". The latch 3 curves at one end to form a generally hook-shaped catch 23 and at an opposite end to form a generally cylindrical figure-eight shaped lower channel 25 for receiving the axis or pin 22, thereby forming a pivot stop 27. Adjacent the pivot and intermediate the lower channel 25 and catch 23 is an upper channel or latch portion 29 for receiving the axis or pin 22 for locking the latch 3 in a closed position, as discussed in greater detail below.

Figure 1:
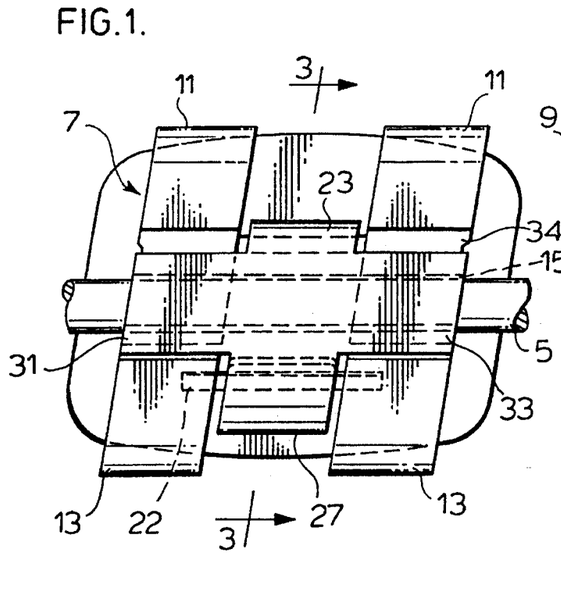
FIG. 1 is a front elevation view of an orthodontic bracket according to the preferred embodiment showing a pivotal latch in the final closed position.
Figure 2:
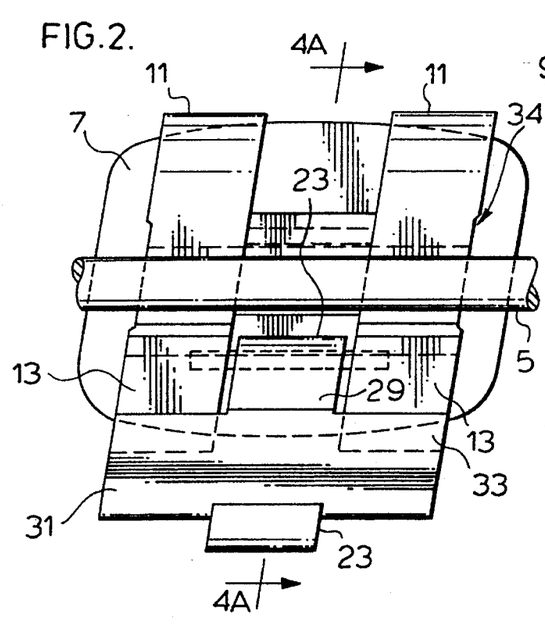
FIG. 2 is a front elevation view of the bracket of FIG. 1 with the pivotal latch in the open position.

As shown in FIGS. 1, 2 and 5, the pivotal latch 3 is of generally cruciform shape from the labial view with mesio-distal arms 31 and 33 for enclosing the slot 15 intermediate respective gingival and occlusal tie wings 11 and 13.

Turning to FIGS. 1 and 3, the pivotal latch 3 is shown in the closed position wherein hook portion 23 is received within groove 17 with a frictional fit between the hook portion 23 and lingual surface 19 and between upper channel 29 and axis or pin 22. In this position, the archwire 5 is securely retained within slot 15. Similarly, with reference to FIGS. 5 and 6, the pivotal latch 3 is shown in the closed position wherein hook portion 23 is frictionally secured against lingual surface 21 and upper channel 29 fictionally engages axis 22 for securing rectangular archwire 5'.

Turning to FIGS. 2 and 4A, the pivotal latch 3 is shown in the open position for removing or installing archwire 5. The space 34 above the pivoting latch allows the gingival edges of the mesial-distal extensions of the latch 3 to move freely upward from the closed to the open position (FIG. 4C). As shown in the sequence of FIGS. 4A, 4B and 4C, the latch 3 may be pivoted at pivot stop 27 around axis or pin 22 for moving from the open position to a closed position wherein the latch 3 covers the slot 15 and the catch 23 is positioned gingivally of the locking surface 19 (solid lines in FIG. 4C, the intermediate positions of FIGS. 4A and 4B being shown in phantom in FIG. 4C). The catch 23 is then pushed downward, or occlusally, to close the latch 3 and move the latch into the upper channel 29.

Figure 7A:
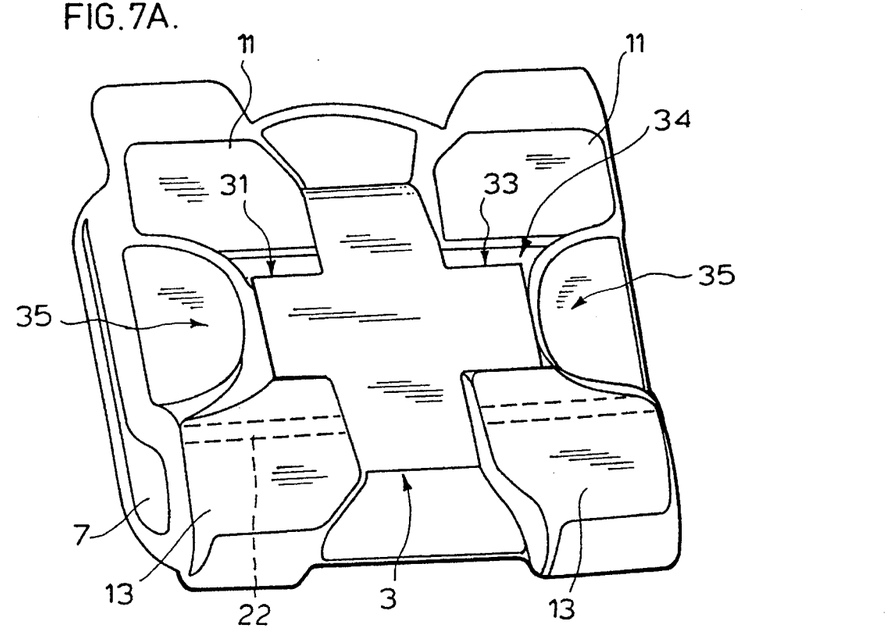
FIG. 7A is a perspective view of a first alternative embodiment of the invention in which mesial and distal ends of the twin bracket body are cut back for allowing increased interbracket distance.
Figure 7B:
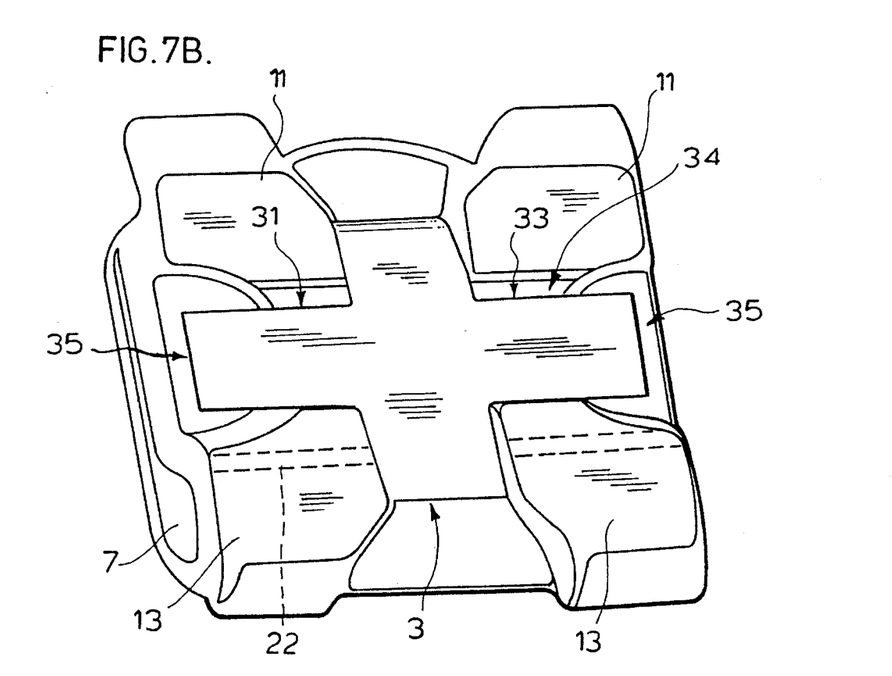
FIG. 7B is a perspective view of a second alternative embodiment of the invention in which the latch is extended mesiodistally.
Figure 8:
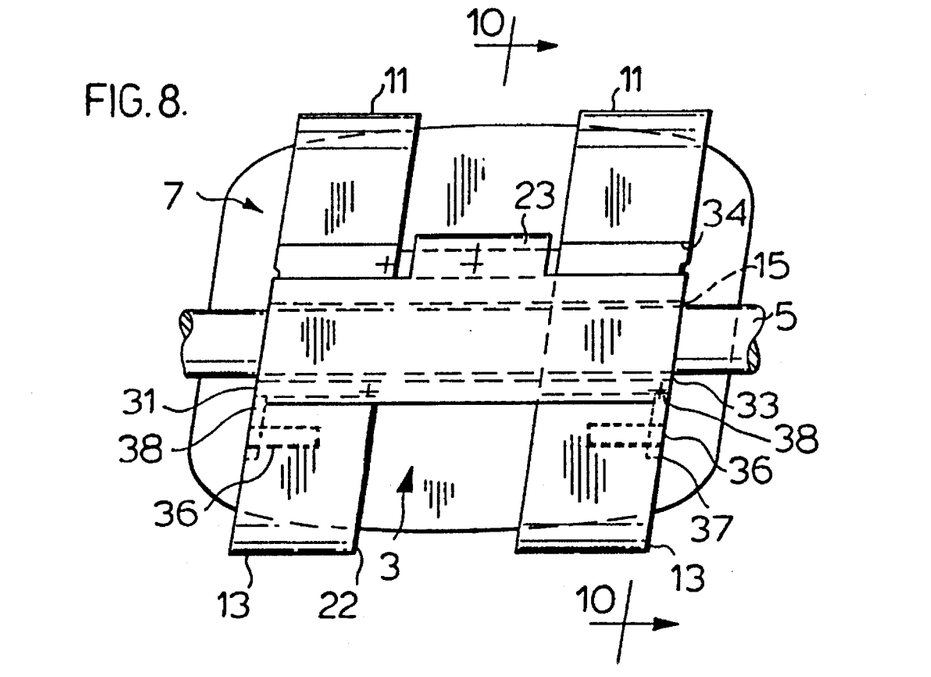
FIG. 8 is a front elevation view of an orthodontic bracket according to a third alternative embodiment showing a modified pivotal latch attached to the side of the bracket mesially and distally at respective insets, in the final closed position.
Figure 9:
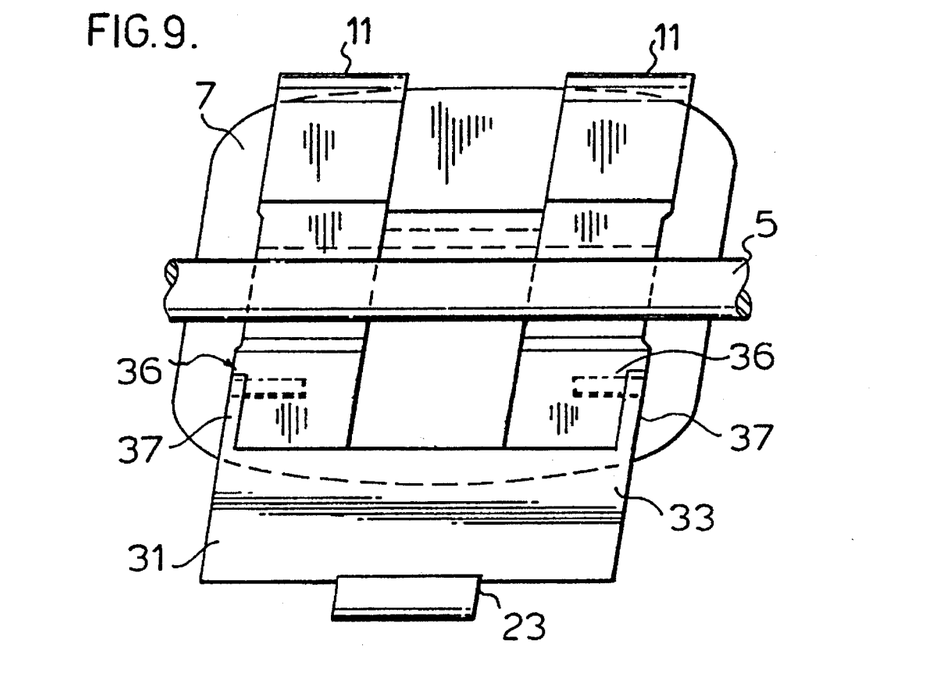
FIG. 9 is a front elevation view of the bracket of FIG. 8 with the modified pivotal latch in the open position.
Figure 10:
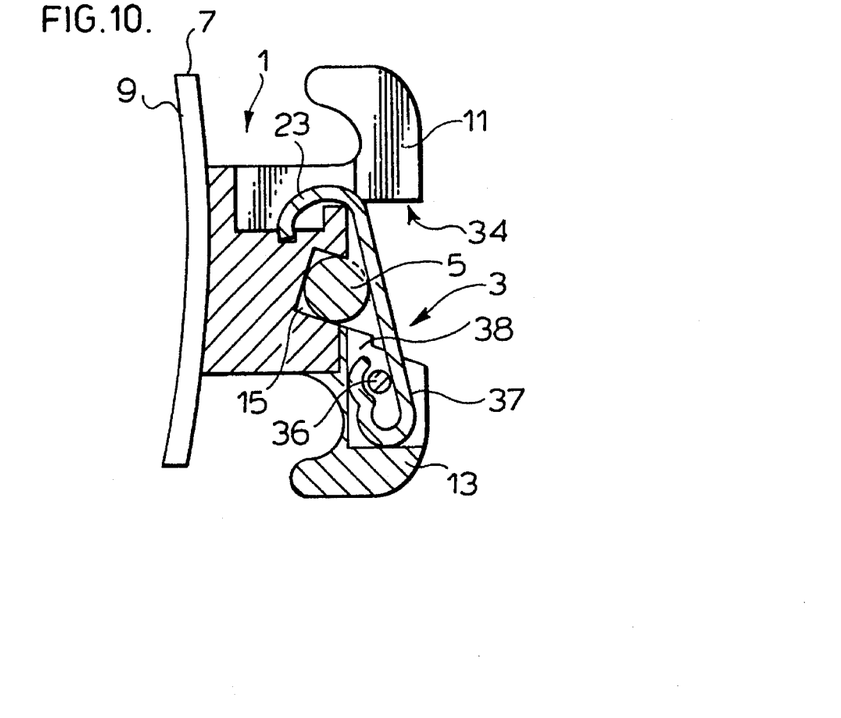
FIG. 10 is a cross-sectional view through the line 10—10 in FIG. 8.
Figure 11:
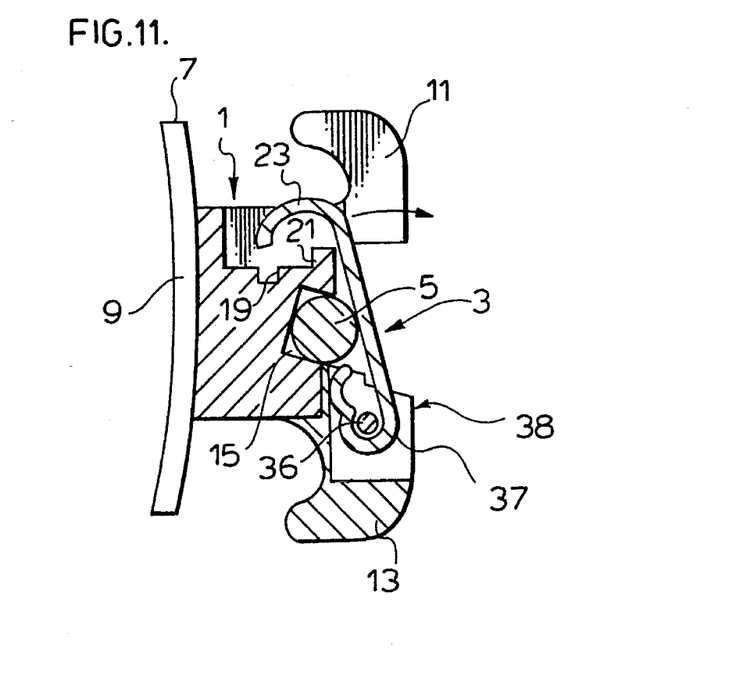
FIG. 11 is a cross-sectional view similar to FIG. 10 with the pivotal latch disengaged.

Turning to the alternative embodiments of FIGS. 7A and 7B, mesial and distal insets 35 are provided in the body portion 1 to provide increased flexibility between the brackets for the archwire 5 or 5' (FIGS. 1–6). This allows for increased interbracket distance. As shown in FIG. 7a, the latch 3 may be provided with short mesio-distal arms 31 and 33, or with long mesio-distal arms 31 and 33 as shown in FIG. 7B.

With reference to FIGS. 8 to 11, a further alternative embodiment is shown wherein the pivoting latch 3 is attached mesiodistally to the external distal ends of pivot axis or pin 22. Specifically, instead of having centrally located upper and lower channels 25 and 29 for receiving a single pivot stop 27 as in the embodiments of FIGS. 1–6, a pair of generally figure-eight shaped laterally positioned pivoting arms 37 are provided in monkey-bar configuration for pivoting around the mesial and distal portions of pivot pin 22. A pair of inset spaces 38 (FIG. 10) are provided in the sides of the bracket body 1 superior to the pivot pin 22, to allow disengagement of the pivoting latch 3 by upward movement of the latch 3.

Figure 12:
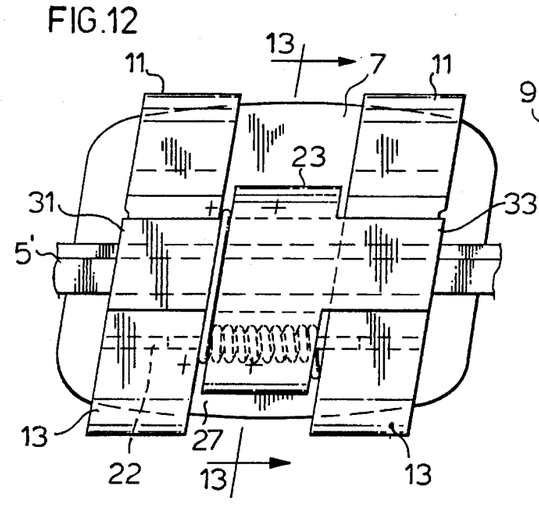
FIG. 12 is a front elevation view of an alternative embodiment with an internal spring-loaded latch.
Figure 13:
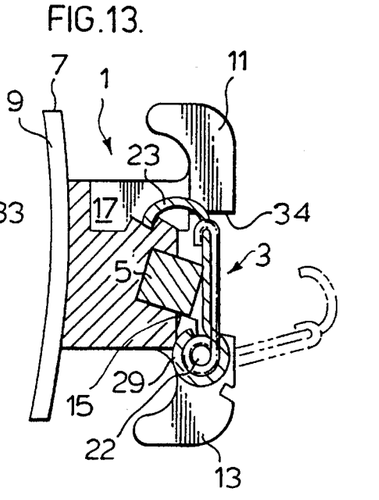
FIG. 13 is a cross-sectional view through the embodiment of FIG. 12.
Figure 14:
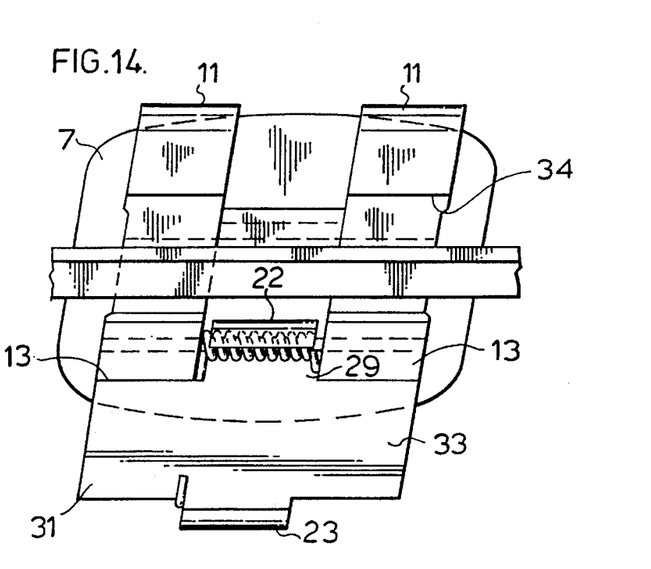
FIG. 14 is a view similar to FIG. 12 with the latch in an open position.

With reference to the embodiment of FIGS. 12 to 14, a spring 42 is wrapped around the pivot pin 22 and the latch 3 is wrapped around the spring to assist the latch in closing forcefully. To open the latch, the catch 23 is lifted up and pivots occlusally to open. To lock the latch in the open slot position, the latch horizontal component occlusal end (frontal view) steps over a lock notch 44.

Figures 15, 16:
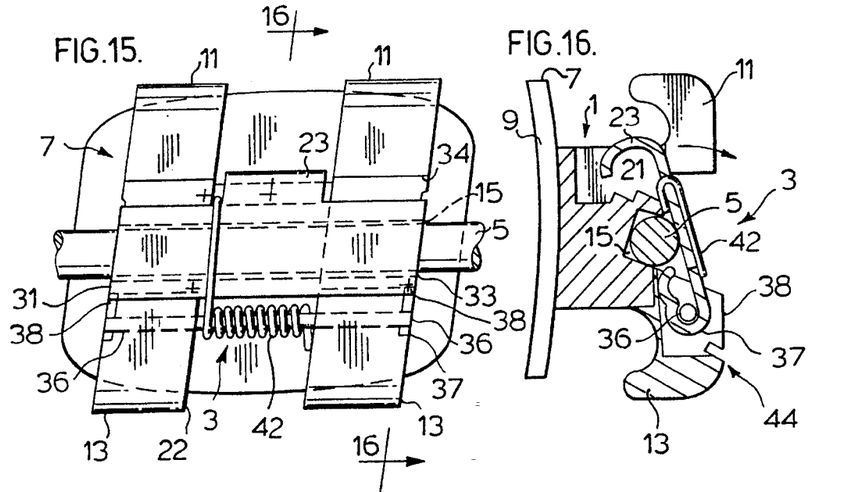
FIG. 15 is a front elevation view of a further alternative embodiment with external spring-loaded latch.
FIG. 16 is a cross-sectional view through the embodiment of FIG. 15.
Figure 17:
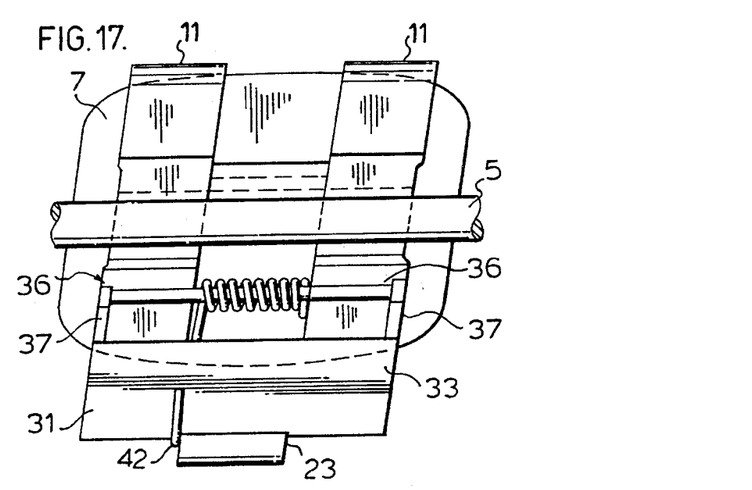
FIG. 17 is a view similar to FIG. 15 with the latch in an open position.

According to the embodiment of FIGS. 15 to 17, the spring 42 is wrapped around the outside of the pivot pin 22 and the pivotal latch continues to be connected to the side of the bracket.

Figure 18A:
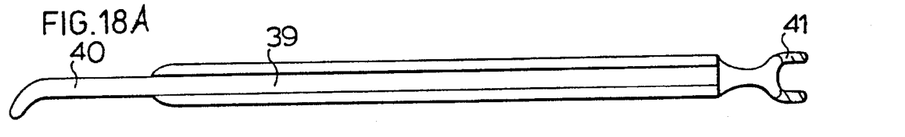
FIGS. 18A and 18B are a side view of a double-sided instrument for use with the bracket according to the present invention, and a detailed view of a right-angle alternative design, rspectively.
Figure 18B:
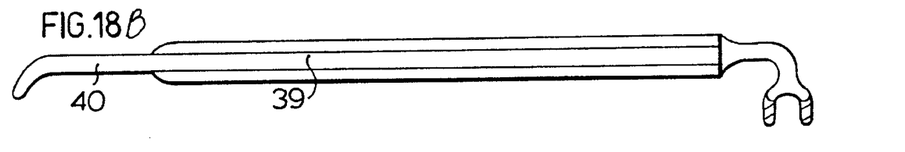

In order to open and close the latch 3, a suitable orthodontic tool is used as shown in FIG. 18. The tool comprises a central body portion 39, a flat generally nose-shaped portion 40 at one end for opening and closing the latch 3, and a generally square corrugated fork-shaped portion 41 at an opposite end for gripping and guiding the archwires lingually deep into the archwire slot to allow easy uninhibited latch closure, especially on rotated teeth. The square corrugated fork-shaped portion can be positioned at an 45° angle to the body of the instrument. In operation, the portion 40 is used to push occlusally on catch portion 23, thereby urging the catch portion 23 into groove 17 such that the latch 3 moves in an occlusal direction and axis or pin 22 is securely received within upper channel 29 in FIGS. 1 and 3 (or pivoting arms 37 in FIGS. 8 and 9). Similarly, in order to unlock the latch 3, portion 40 of the surgical tool is used to push gingivally on pivot stop 27 in the embodiment of FIGS. 1–6, 7A and 7B, so that the latch 3 moves in a gingival direction for receiving axis or pin 22 in pivot stop 27 and lifting the catch portion 23 out of groove 17 (or 21). In the embodiments of FIGS. 8–11, 12–14 and 15–17, the same procedure is followed except upward pressure is applied instead on the semi-rigid flat mid-portion of the latch between the mesial and distal tie wings 11 and 13.

The embodiments of the invention discussed herein are directed to a upper bracket. The same principles apply for an lower bracket in which case the gingival-occlusal orientation is reversed.

In summary, a self-engaging twin edgewise orthodontic bracket is provided which enjoys the advantages of a pivotal latch as well as the advantages of gingival-occlusal movement of the latch for locking and unlocking. The pivotal latch is advantageous over a sliding shutter, such as described in my co-pending application U.S. Ser. No. 08/007,095, since the clinician is given more open access to the bracket for opening, closing and cleaning, etc. By providing a degree of gingival-occlusal movement of the latch, opening, closing and locking of the latch is made easier and more reliable than prior art pivotal latches such as disclosed in U.S. Pat. Nos. 4,634,662 and 4,712,999.

Other embodiments and variations of the invention are possible. For example, although the first and second lingual locking surfaces 19 and 21 are shown as a groove 7 and a step, respectively, the lingual locking surfaces may be implemented as a pair of grooves, a pair of steps, or other suitable geometry. The generally figure-eight shaped pivotting arms may be either lingual or labial. Also, for illustrative purposes, the bracket of the present invention is shown configured for a maxillary tooth, although a variation in orientation allows the invention to be used on a mandibular teeth. The bracket of the present invention may be fabricated from metal, plastic, ceramic or any suitable material. All such modifications and variations are believed to be within the sphere and scope of the present invention as defined by the claims appended hereto.

I claim:

1. A self-engaging twin edgewise orthodontic bracket, comprising:

a body portion having a lingual surface for attachment to a tooth, a pair of gingival and occlusal tie wings extending buccal-labially from said lingual surface, a central mesiodistally extending labially opening slot for receiving an archwire, a first mesiodistally extending lingual locking surface intermediate one of either said gingival or occlusal tie wings, and mesiodistally extending axis means intermediate the other of said one of either said gingival or occlusal tie wings; and a pivotal latch having catch means at one end thereof for locking engagement with said locking surface, lingually open figure-eight shaped pivot means at an opposite end thereof defining first and second channels, said first channel for pivotally receiving said axis means such that said latch is pivotal from an open position for installing and removing said archwire to a closed position wherein said latch covers said slot and said catch means is positioned gingivally of said locking surface, and said second channel for receiving said axis means such that said catch means securely engages said locking surface in said closed position thereby securely retaining said archwire in said slot.

2. The self-engaging twin edgewise orthodontic bracket of claim 1, further comprising a second mesiodistally extending lingual locking surface disposed labially of said first locking surface for securely engaging said catch means when said axis means is received in said second channel, whereby said latch is retained in said closed position in a more labial aspect than when said catch means engages said first locking surface.

3. The self-engaging twin edgewise orthodontic bracket of claim 1, wherein said catch means is generally J-shaped.

4. The self-engaging twin edgewise orthodontic bracket of claim 1, wherein said axis means is a generally cylindrical pin extending between said other of said one of either said gingival or occlusal tie wings.

5. The self-engaging twin edgewise orthodontic bracket of claim 1, further comprising a mesiodistally extending groove for receiving said catch means in the closed position, wherein said first locking surface forms a lingual face of said groove.

6. The self-engaging twin edgewise orthodontic bracket of claim 1, wherein said pivotal latch is generally cruciform shaped when viewed labially with mesiodistal arms for enclosing said slot intermediate respective gingival and occlusal tie wings.

7. The self-engaging twin edgewise orthodontic bracket of claim 6, wherein said catch means extends perpendicular to said arms at said one end and curves in the form of a generally J-shaped hook.

8. The self-engaging twin edgewise orthodontic bracket of claim 6, wherein said pivot means extends perpendicular to said arms at said opposite end and curves to form said first channel, said first channel thus formed being generally cylindrical.

9. The self-engaging twin edgewise orthodontic bracket of claim 8, wherein said latching means extends parallel to said first generally cylindrical channel and curves lingually to form said second channel, said second channel thus formed being generally semicircular.

10. The self-engaging twin edgewise orthodontic bracket of claim 6, wherein said lingually open figure-eight shaped pivot means further comprises a pair of generally figure-eight shaped perpendicular extensions from distal ends of said arms at said opposite end of said pivotal latch in monkey-bar configuration, each of said extensions curving respectively to form said first channel, said first channel thus formed being generally cylindrical.

11. The self-engaging twin edgewise orthodontic bracket of claim 10, wherein said latching means extends parallel to said first generally cylindrical channel in each of said extensions and curves lingually to form said second channel in each of said extensions, said second channel thus formed being generally semicircular.

12. The self-engaging twin edgewise orthodontic bracket of claim 1, wherein said body portion includes a pair of mesial and distal insets to provide increased flexibility between the brackets for said archwire thereby allowing for increased interbracket distance.

13. The self-engaging twin edgewise orthodontic bracket of claim 1 further including spring means connected to said pivot means for assisting in firm closure of said pivotal latch.

14. The self-engaging twin edgewise orthodontic bracket of claim 13, wherein said pivotal latch overlays said spring means.

15. The self-engaging twin edgewise orthodontic bracket of claim 14 further including a lock notch for locking said pivotal latch in the open position.

* * * * *